United States Patent
Tidwell et al.

(10) Patent No.: US 6,780,189 B2
(45) Date of Patent: Aug. 24, 2004

(54) SURGICAL INSTRUMENT WITH A COLLET LOCKING AND INDEXING SYSTEM

(75) Inventors: Durrell G. Tidwell, Burleson, TX (US); Rex Wesley Shores, The Colony, TX (US)

(73) Assignee: Medtronic, Inc., Minneapolis, MN (US)

( * ) Notice: Subject to any disclaimer, the term of this patent is extended or adjusted under 35 U.S.C. 154(b) by 35 days.

(21) Appl. No.: 10/164,880

(22) Filed: Jun. 7, 2002

(65) Prior Publication Data

US 2003/0229351 A1 Dec. 11, 2003

(51) Int. Cl.[7] .............................................. A61B 17/16
(52) U.S. Cl. ........................................ 606/80; 606/170
(58) Field of Search ............................ 606/79, 80, 81, 606/167–173, 176–180; 279/143, 145, 144; 408/124; 409/231

(56) References Cited

U.S. PATENT DOCUMENTS

| | | | |
|---|---|---|---|
| 2,719,722 A | * | 10/1955 | Nickless |
| 2,807,473 A | | 9/1957 | Kiehne |
| 2,931,659 A | * | 4/1960 | Novkov |
| 4,699,550 A | | 10/1987 | Baker |
| 5,222,956 A | | 6/1993 | Waldron |
| 5,330,480 A | | 7/1994 | Meloul et al. |
| 5,347,988 A | | 9/1994 | Hori |
| 5,380,333 A | | 1/1995 | Meloul et al. |
| 5,490,683 A | | 2/1996 | Mickel et al. |
| 5,505,737 A | | 4/1996 | Gosselin et al. |
| 5,569,256 A | | 10/1996 | Vaughn et al. |
| 5,601,560 A | | 2/1997 | Del Rio et al. |
| 5,630,818 A | | 5/1997 | Del Rio et al. |
| 5,741,263 A | | 4/1998 | Umber et al. |
| 5,779,404 A | | 7/1998 | Jore |
| 5,782,836 A | | 7/1998 | Umber et al. |
| 5,833,704 A | | 11/1998 | McCombs et al. |
| 5,888,200 A | | 3/1999 | Walen |
| 5,893,851 A | | 4/1999 | Umber et al. |
| 5,904,687 A | | 5/1999 | Del Rio et al. |
| 5,928,238 A | | 7/1999 | Scarborough et al. |
| 5,928,241 A | | 7/1999 | Menut et al. |
| 5,941,891 A | | 8/1999 | Walen |
| 5,989,257 A | | 11/1999 | Tidwell et al. |
| 5,993,453 A | | 11/1999 | Bullara et al. |
| 5,993,454 A | | 11/1999 | Longo |
| 6,033,408 A | | 3/2000 | Gage et al. |
| 6,062,575 A | | 5/2000 | Mickel et al. |
| 6,209,886 B1 | | 4/2001 | Estes et al. |
| 6,270,087 B1 | | 8/2001 | Mickel et al. |
| RE37,358 E | | 9/2001 | Del Rio et al. |

* cited by examiner

Primary Examiner—David O. Reip
(74) Attorney, Agent, or Firm—Haynes and Boone, LLP

(57) ABSTRACT

A surgical instrument is provided for cutting bone and other tissue. The surgical instrument includes a motor assembly, a collet, a locking nut, and an attachment. The motor assembly includes a cavity having a groove on an inner surface that corresponds to a groove on an outer surface of the collet. The corresponding grooves form an aperture when the collet is inserted into the cavity. The insertion of a pin into the aperture prevents rotation of the collet relative to the cavity. The locking nut is placed over the collet and fastened to the motor assembly to secure the collet to the motor assembly. The attachment is fastened to the collet by placing protuberances on the attachment into corresponding apertures on the collet. The consistent alignment provided by the locking and indexing system enables the motor assembly and attachment to receive alignment markings before the surgical instrument is assembled.

23 Claims, 6 Drawing Sheets

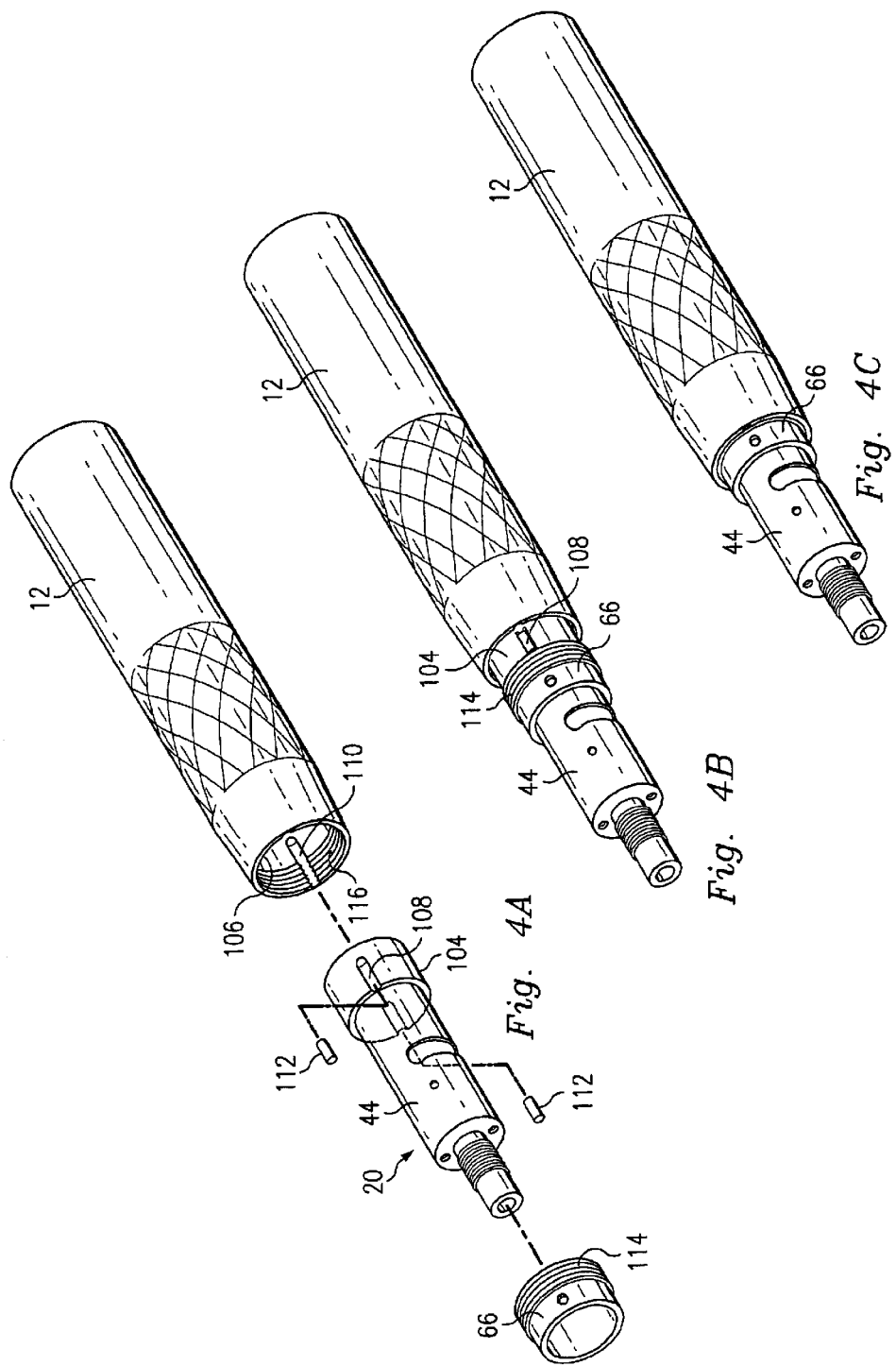

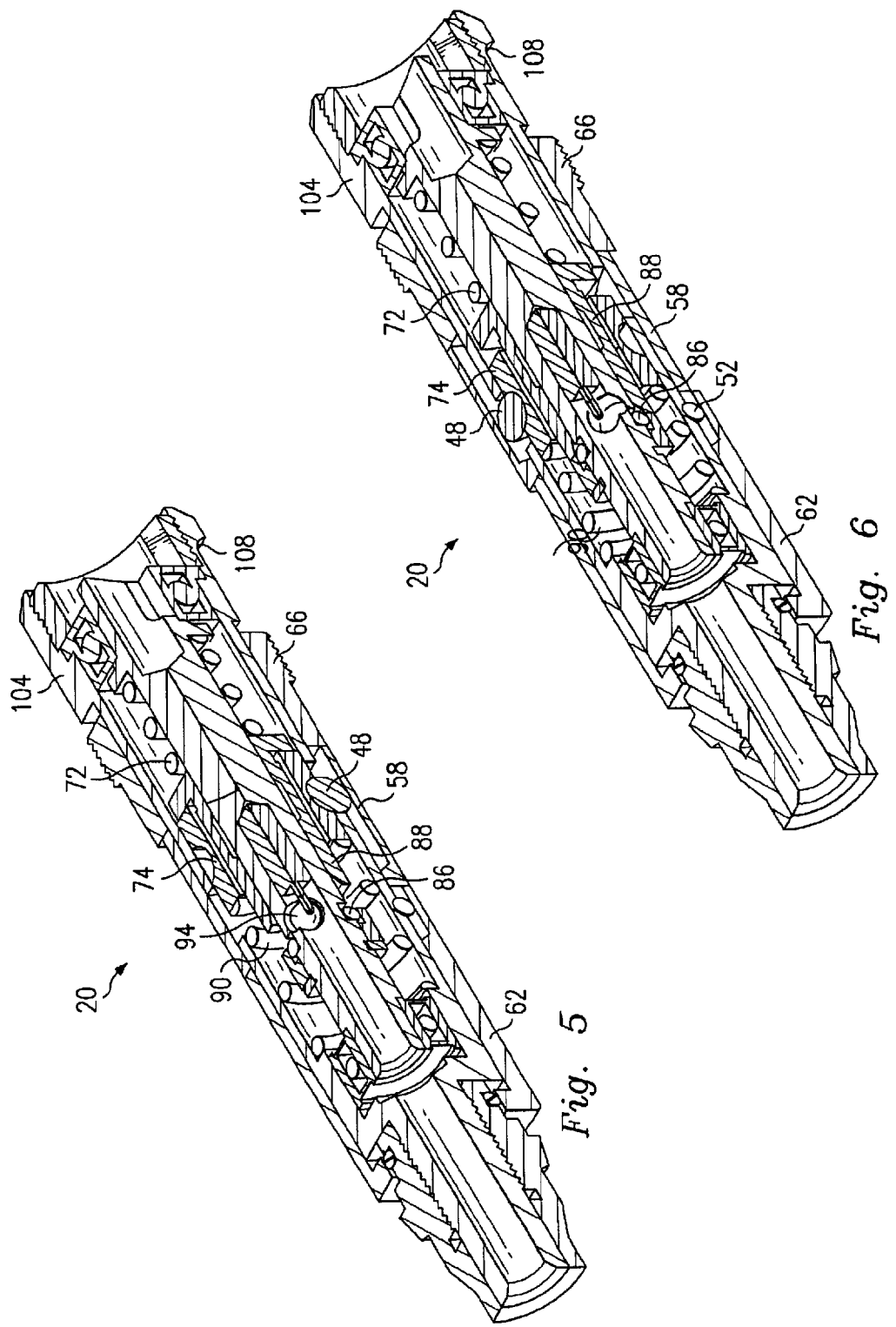

SURGICAL INSTRUMENT WITH A COLLET LOCKING AND INDEXING SYSTEM

CROSS REFERENCE

The following related patent applications are hereby made of record and incorporated by reference: U.S. patent Ser. No. 10/102,762, U.S. patent Ser. No. 09/303,781, and U.S. patent Ser. No. 60/352,609.

FIELD OF THE INVENTION

The present disclosure generally relates to surgical instruments and their use. More particularly, the present disclosure relates to a collet locking and indexing system for surgical instruments.

BACKGROUND

Surgical instruments, in general, should satisfy several requirements in order to fulfill their various roles during surgery. One requirement is that certain components of a multi-part instrument, such as an instrument used for dissecting bone or tissue, should be aligned properly when the instrument is assembled. For example, alignment-sensitive components forming the instrument should be in certain positions relative to the other components when the instrument is originally assembled. Thereafter, each time the instrument is reassembled after being disassembled, each of the alignment-sensitive components should be returned to the same relative position. Among other benefits, consistent alignment ensures that the instrument is correctly positioned to receive a surgeon's hand in an optimal manner. Such optimal alignment may take into account such factors as the location of any controls and the angle of a tool associated with the instrument, such as a cutting tool. If the alignment of the various components is not correct, a surgeon may be unable to access the controls when the cutting tool is properly positioned.

Typically, to ensure that the instrument is properly aligned, marks are placed on the exterior of the instrument in the following manner. The instrument, which often includes a locking device such as a collet, a motor and motor assembly, and an attachment, is fully assembled. The assembly process includes attaching the collet to the motor assembly, sliding the attachment over the collet, and securing the attachment to the collet. Marks may then be made on the exterior of the motor assembly and the attachment to indicate their relative positions ("locked" or "unlocked") when the instrument is fully assembled. To attach a cutting tool, the attachment is loosened (moved to the "unlocked" position), the collet is opened and the tool is inserted into the collet. The collet is then closed to securely retain the tool and the attachment is tightened until the mark on the attachment is aligned with the corresponding mark on the motor assembly (the "locked" position). Accordingly, the alignment marks prevent the attachment from being over-tightened, which could damage the instrument, and from not being tightened enough, which could have disastrous consequences during surgery. As the alignment marks depend on the relative positions of the attachment, motor assembly, and collet, these components play an important role in the alignment process.

While frequently used, this post-assembly marking process presents a number of difficulties. For example, when one of the alignment-sensitive components in the instrument must be replaced, the instrument will likely need to be remarked. For example, if the collet must be replaced, the original collet must be removed and a new collet must be attached to the motor assembly. However, the likelihood that the new collet will accept the original attachment in exactly the same manner is doubtful. For example, if the motor assembly and the collet are threaded, there is very little likelihood that the threads of the new collet will engage the threads of the motor assembly in the exact manner as the old collet. Accordingly, the new collet will not be in the same position relative to the motor assembly as the old collet. Therefore, when the attachment is connected to the new collet, it is unlikely that the mark on the attachment will properly align with the mark on the motor assembly. As the markings are often permanent, one or more components that are otherwise perfectly functional may be discarded and replaced with unmarked components that can be marked appropriately.

Therefore, what is needed is a locking and indexing system that enables various alignment-sensitive components of a surgical instrument to be assembled in a consistent manner, allowing alignment markings to be placed on components before the instrument is assembled.

SUMMARY

The present disclosure provides many technological advances that can be used, either alone or in combination, to provide an improved powered surgical instrument and/or an improved system and method for using powered surgical instruments.

In one embodiment, a locking system for a surgical instrument is provided. The locking system includes a collet having a first engagement element that corresponds with a second engagement element of a motor assembly. The first and second engagement elements prevent rotation of the collet relative to the motor assembly. The locking system also includes a slidable locking member operable to secure the collet to the motor housing.

In another embodiment, the first and second engagement elements are apertures operable to form a cavity around a rigid fastening member. In still another embodiment, one of the first and second engagement elements is a protuberance and the remaining first or second engagement element is an aperture operable to receive the protuberance.

In yet another embodiment, a surgical instrument is provided. The surgical instrument includes a collet including a first engaging means and a motor assembly operable to receive the collet in a cavity. The cavity includes a second engaging means operable to engage the first engaging means to prevent rotation of the collet relative to the motor housing. The surgical instrument also includes a locking element operable to secure the collet to the motor assembly.

In still another embodiment, a collet for insertion into a cavity of a surgical instrument is provided. The collet includes a distal portion having an opening for receiving a tool and a first fastening element for accepting an attachment. The collet also includes a proximal portion with a first alignment element for engaging a second alignment element present in the cavity. A locking member is included for securing the collet to the surgical instrument.

Further forms and embodiments of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present disclosure will become more fully understood from the detailed description and the accompanying drawings, wherein:

FIGS. 4A and 4B are partially exploded views of the surgical instrument of FIGS. 2A–2C and 3.

FIG. 4C is an assembled perspective view of the surgical instrument of FIGS. 4A and 4B.

FIG. 5 is a partial quarter-section perspective view of a portion of the surgical dissection tool of FIG. 3 illustrating the unlocked position.

FIG. 6 is a partial quarter-section perspective view of a portion of the surgical dissection tool of FIG. 5 rotated 90° illustrating the locked position.

DETAILED DESCRIPTION

Figure 1:
FIG. 1 is an environmental view of a surgical instrument for the dissection of bone and other tissue according to the teachings of a preferred embodiment of the present disclosure operatively associated with a patient for performing a craniotomy.

The present disclosure relates to surgical tools, and more particularly, to a collet locking and indexing system for surgical instruments. It is understood, however, that the following disclosure provides many different embodiments, or examples, for implementing different features of the invention. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Referring initially to FIG. 1, a surgical instrument for the dissection of bone and other tissue constructed in accordance with the teachings of a first preferred embodiment is illustrated and generally identified at reference numeral 10. The surgical instrument 10 is shown operatively associated with a patient A for performing a craniotomy. It will become apparent to those skilled in the art that the described instrument is not limited to any particular surgical application but has utility for various applications in which it is desired to dissect bone or other tissue. Additional applications include:

1. Arthroscopy—Orthopaedic
2. Endoscopic—Gastroenterology, Urology, Soft Tissue
3. Neurosurgery—Cranial, Spine, and Otology
4. Small Bone—Orthopaedic, Oral-Maxiofacial, Ortho-Spine, and Otology
5. Cardio Thoracic—Small Bone Sub-Segment
6. Large Bone—Total Joint and Trauma
7. Dental.

Figure 2:
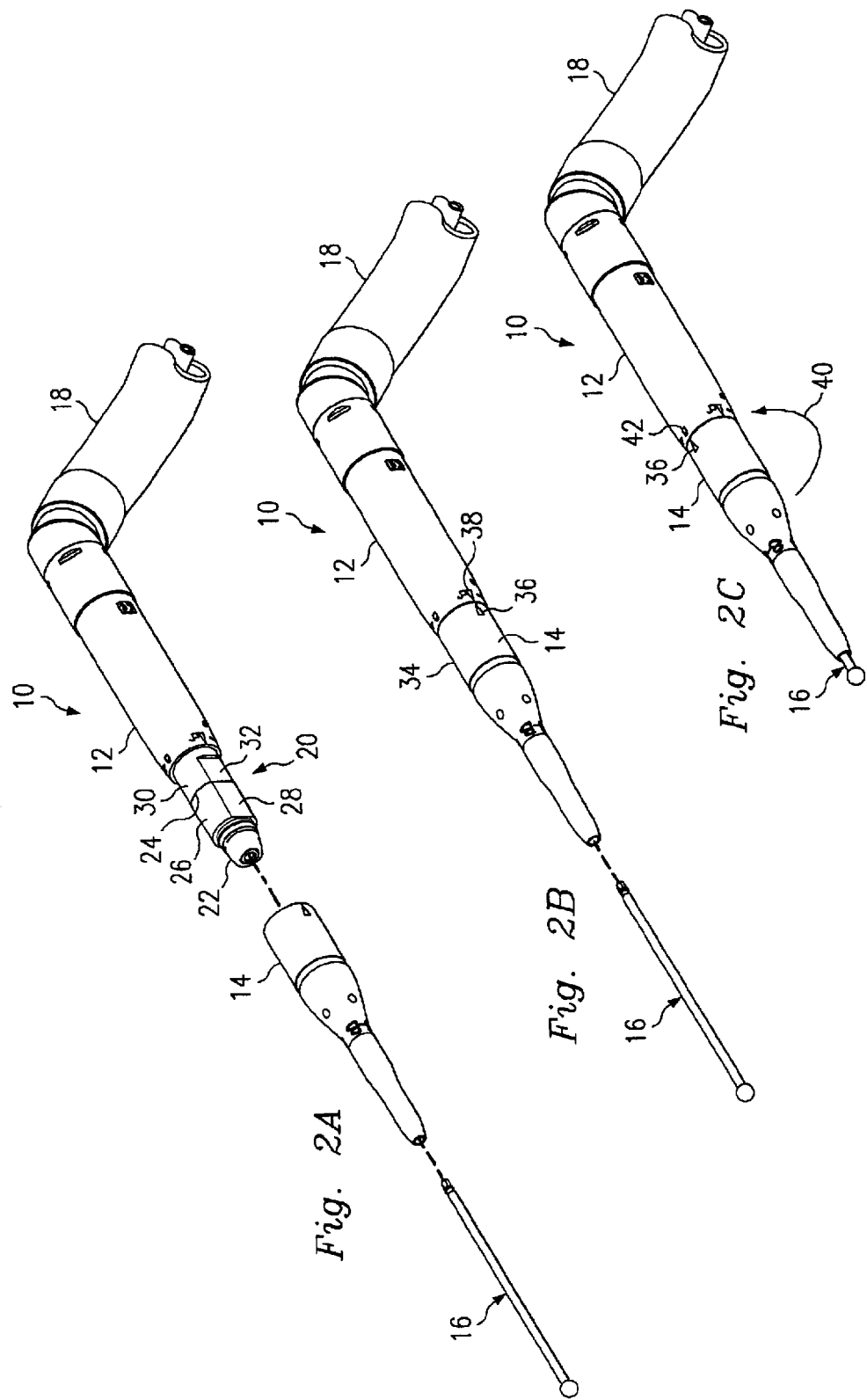
FIG. 2A is a partially exploded perspective view of a surgical dissection tool according to the present disclosure.
FIG. 2B is a partially exploded perspective view of the surgical dissection tool of FIG. 2A.
FIG. 2C is an assembled perspective view of the surgical dissection tool of FIG. 2A.

With reference to FIGS. 2A–2C, the surgical instrument 10 is illustrated to generally include a motor assembly 12, an attachment 14, and a surgical tool 16. The attachment 14 may provide a gripping surface for use by a surgeon and may also shield underlying portions of the instrument 10 during a surgical procedure. In a preferred embodiment, the surgical tool 16 is a cutting tool or dissection tool, although the type of tool is not essential to implementing the present disclosure.

The surgical instrument 10 is shown connected to a hose assembly 18 for providing a source of pressurized fluid (e.g., air) to the motor assembly 12 and venting exhaust air away from the surgical site. In the exemplary embodiments that will be described, the surgical instrument 10 is pneumatically powered. It is further understood, however, that many of the teachings discussed herein will have equal application for an electrically powered surgical instrument.

As shown in FIG. 2A and described later in greater detail, the motor housing 12 includes a coupling assembly 20 with a tapered leading portion 22 and a Double D region comprising a pair of opposed and substantially parallel planar portions interrupting the cylindrical body to define two opposed substantially parallel cylindrical portions. These portions are separated by junction 24 into an axially translatable segment having cylindrical portion 26 and flat portion 28, and a rotatably translatable segment having cylindrical portion 30 and flat portion 32.

Referring now to FIG. 2B, attachment housing 14 includes an internal cavity (not shown) adapted and configured to engage coupling assembly 20 of motor assembly 12. In an initial position with first cylindrical portion 34 substantially abutting motor assembly 12, attachment indicator mark 36 is in substantial alignment with unlocked indicator mark 38 on the motor assembly. In this position, dissection tool 16 may be inserted into attachment housing 14 and be received in the coupling assembly 20 within motor assembly 12. Referring now to FIG. 2C, with dissection tool 16 inserted within attachment housing 14 and engaged in the coupling assembly 20, attachment housing 14 may be rotated in the direction of arrow 40 with respect to motor assembly 12. Movement in this direction moves attachment indicator marking 36 into substantial alignment with the locked indicator marking 42 on motor assembly 12. Such movement also operates the coupling assembly 20 to lock dissection tool 16 into driving engagement with the internal motor.

In the present embodiment, the motor assembly 12, attachment 14, and coupling assembly 20 are designed so that indicator marks 36, 38, 42 may be placed on attachment 14 and motor assembly 12 at the component level (e.g., before assembly) rather than the assembly level. The ability to add the indicator marks 36, 38, 42 at the component level provides a number of advantages. For example, the indicator marks 36, 38, 42 (and other labeling or lettering) are typically either scratched or laser etched onto the surface of the motor assembly 12 and attachment 14. Both of these methods may produce a white or metallic marking on the anodized surface. Using scratching or laser etching, the marking can be applied at either the component level or the assembled level. However, some color schemes (such as black markings on a gold anodized surface) may be difficult or impossible to achieve once assembly of the instrument is completed and so the markings should be made at the component level. For example, the markings may be stamped onto a surface of a component using a force that may damage an assembled instrument.

Figure 3:
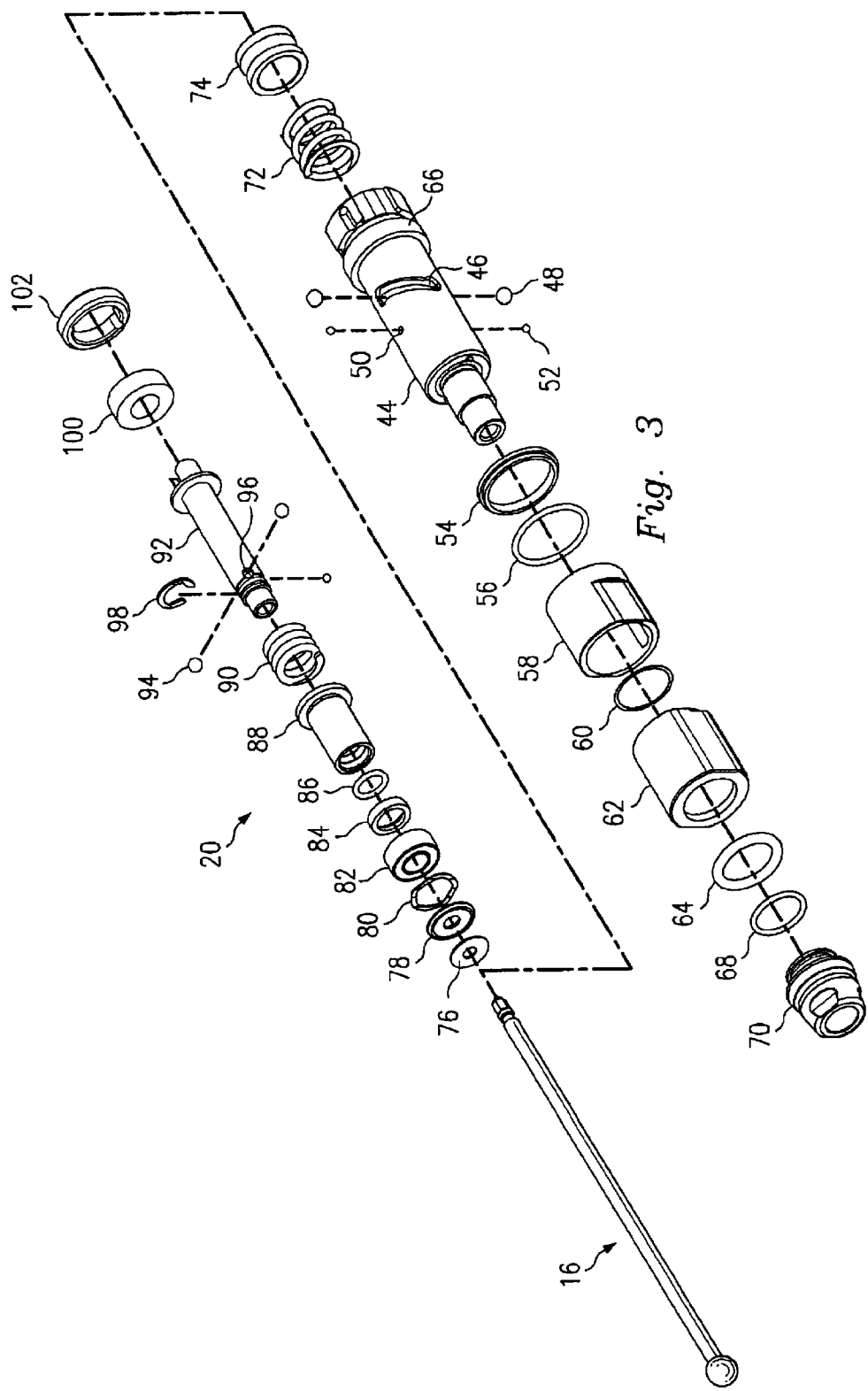
FIG. 3 is an exploded perspective view of a portion of the surgical dissection tool of FIGS. 2A–2C.

Referring now to FIG. 3, one embodiment of the coupling assembly 20 of FIGS. 2A–2C that may be used to overcome the marking difficulties previously described is shown in detail. The coupling assembly 20 includes a locking nut 66 positioned on a collet housing 44. The collet housing 44 has a helical slot 46 adapted to receive ball bearings 48, and a pair of apertures 50 adapted to receive alignment balls 52. Coupling assembly 20 further includes a housing spacer 54 and an O-ring 56 associated with posterior Double D-collet 58. Posterior Double D-collet 58 is spaced from anterior Double D-collet 62 by shim 60. The assembly further includes O-rings 64 and 68 and tapered nose 70. A number of the remaining components are disposed within collet housing 44. More specifically, spring 72 and ball carrier 74, along with additional components washer 76, seal 78, wave spring 80, bearing tube 82, sleeve keeper 84 and O-ring 86 are assembled within collet housing 44. Coupling assembly 20 also includes hex closure sleeve 88, spring 90, rotor shaft 92, and ball bearings 94 retained in openings 96 in the rotor shaft by retaining ring 98. This internal assembly is completed by bearing 100 and lock ring 102.

Referring now to FIGS. 4A–4C, in one embodiment, the coupling assembly 20 may be attached to the motor assembly 12 as follows. It is understood in the following example that the coupling assembly 20 is represented only by the collet housing 44 for purposes of clarity, but the coupling assembly 20 may include other components as illustrated in FIG. 3. The coupling assembly 20 includes a base 104 sized for insertion into a cavity 106 of the motor assembly 12. The base 104 includes one or more apertures 108 that extend from the distal end of the base 104 (relative to the motor assembly 12) towards the proximal end of the base 104. However, the apertures 108 do not extend the entire length of the base 104.

The cavity 106 in the motor assembly 12 includes one or more apertures 110 that correspond to the apertures 108 of the coupling assembly 20. Accordingly, a pin 112 may be placed in each aperture 108 of the coupling assembly 20 before the coupling assembly 20 is inserted into the cavity 106. The pins 112 may then be aligned with the apertures 110 of the motor assembly 12 and the coupling assembly 20 may be inserted into the motor assembly 12. As the proximal end of the base 104 is not grooved, the pins 112 will not extend past the base 104. Once inserted, the pins 112 serve to align the coupling assembly 20 and the motor assembly 12 and also prevent the coupling assembly 20 from rotating within the motor assembly 12. In addition, the pin and groove arrangement provides sufficient structural strength to survive the loading created by the rotation of the tool 16 during surgery. Removal of the coupling assembly 20 will remove the pins 112.

It is understood that alternate methods of assembly may be desirable. For example, before placing the pins 112 into the apertures 108, the coupling assembly 20 may be inserted into the motor assembly 12 and rotated to align the apertures 108, 110. When this is achieved, the matching grooves will be accessible via the origination points of the apertures 108, 110 in the distal portion of the base 104 and the motor assembly 12, respectively. The pins 112 may then be inserted into each pair of aligned apertures 108, 110.

Regardless of the assembly procedure used for alignment, after the coupling assembly 20 is inserted into the cavity 106, the locking nut 66 may be used to secure the coupling assembly 20 to the motor assembly 12 as follows. The locking nut 66 includes a plurality of threads 114 that mate with corresponding threads 116 on the motor assembly 12. In the present embodiment, the distal end of the base 104 has a larger diameter than the remainder of the coupling housing 44. The interior diameter of the locking nut 66 is sized so that the locking nut 66 may slide over the coupling assembly 20 until it reaches the base 104, which serves as a lip that prevents the locking nut 66 from further movement in the direction of the motor assembly 12. The threads 114 of the locking nut 66 may then engage the threads 116 of the motor assembly 12 and the locking nut 66 may be rotated until the coupling assembly 20 is secured to the motor assembly 12. Once in place, the locking nut 66 covers the exposed apertures 108 in the base 104. Accordingly, the locking nut 66 serves to both fasten the coupling assembly 20 to the motor assembly 12 and to retain the pins 112 in the apertures 108, 110.

Using the pin and aperture arrangement described above ensures that the coupling assembly 20 may be attached to the motor assembly 12 with a known alignment. As will be described later, this predictable alignment between the coupling assembly 20 and the motor assembly 12 enables the attachment 14 to be aligned predictably with the motor assembly 12.

Figure 7:
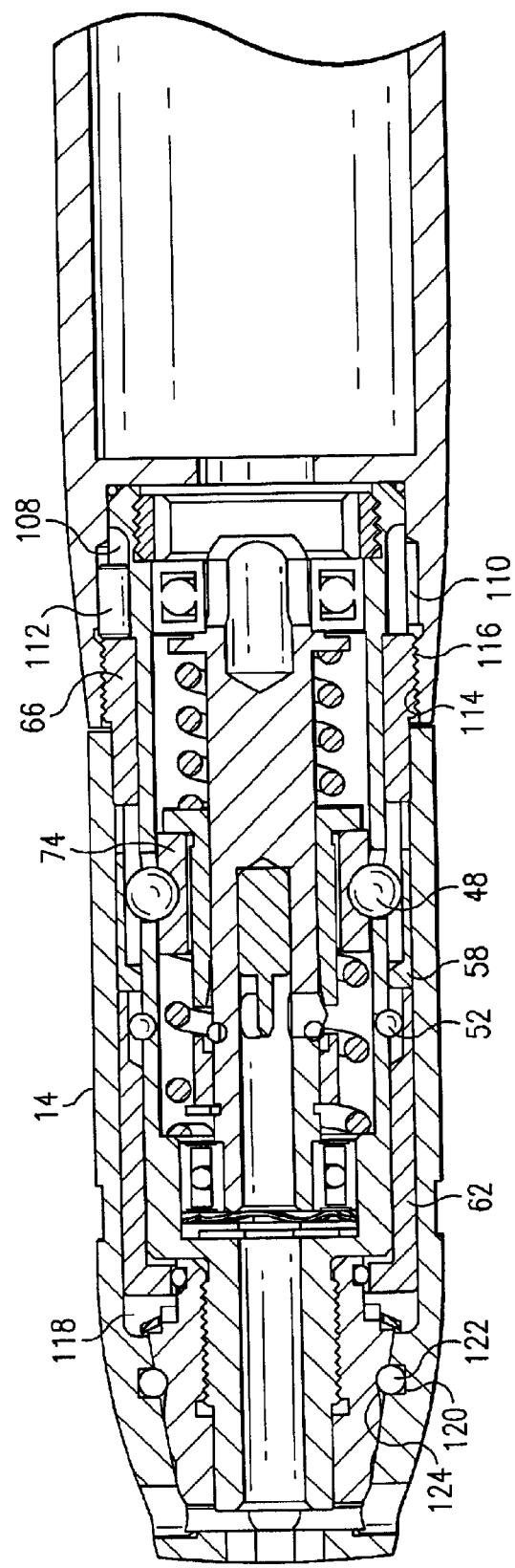
FIG. 7 is a partial cross-section view of a portion of the surgical dissection tool of FIG. 6 illustrating the locked position

Referring again to FIG. 3 and with additional reference to FIGS. 5–7, the coupling assembly 20 of FIG. 4 is shown in cross-section and quarter-section in its assembled configuration while unlocked (FIG. 5) and locked (FIGS. 6 and 7).

Referring particularly to FIG. 5, coupling assembly 20 is shown in the unlocked position. Ball 48 is positioned in helical groove 46 in the proximal position. Ball 48 rides in ball carrier 74 and is moved by ball 48 to the proximal position shown in FIG. 5. In the proximal position, ball carrier 74 urges closure sleeve 88 to compress spring 72 and permits spring 90 to expand to a relaxed position. In the unlocked proximal position, closure sleeve 88 is moved away from locking ball 94 permitting it to move at least partially out of hole 96. However, o-ring 86 tends to urge locking ball 94 into hole 96. This arrangement provides positive positioning of locking ball 94 in hole 96 and into an aperture (not shown) in tool 16, providing tactile feedback to the user that tool 16 is properly positioned in coupling assembly 102.

Referring particularly to FIGS. 6 and 7, after the dissection tool 16 has been properly positioned in coupling assembly 20, proximal Double D collet 58 may be rotated with respect to the other elements of the housing to urge ball 48 and ball carrier 74 to their distal, locking position. FIGS. 6 and 7 shows coupling assembly 20 with proximal Double D collet 58 and balls 48 shown in the position of FIG. 5 and the remaining elements rotated approximately 90°. It will be understood that in operation of the illustrated preferred embodiment, proximal Double D collet 58 and balls 48 are moved while the other elements remain stationary. During the closure operation, as ball carrier 74 advances distally, spring 90 is compressed and spring 72 is allowed to expand. As spring 72 expands, it urges closure sleeve 88 distally. Internal taper surface of closure sleeve 88 engages locking ball 94 and urges it into locking engagement with the aperture (not shown) located on the tool 16. Closure sleeve 88 continues to advance over locking ball 94 to securely hold locking ball 94 in the aperture, thereby inhibiting movement of dissection tool 16 along the longitudinal axis.

Referring still to FIG. 7, attachment housing 14 is adapted to engage the coupling assembly 20 in an interference fit. Further, attachment housing 14 and coupling assembly 20 are configured to provide the user with tactical feedback indicating positive engagement. More specifically, attachment housing 14 includes an internal cavity 118 having a configuration substantially matching the external configuration of coupling assembly 20. The cavity 118 includes an internal annular groove 120 carrying an O-ring 122. Coupling assembly 20 defines an external annular groove 124 adapted to receive a portion of O-ring 122. Thus, it will be understood that as attachment housing 14 is advanced over coupling assembly 20, O-ring 122 will be slightly compressed into groove 120 as it engages tapered front end 22 to an expanded inner diameter. When O-ring 122 is positioned over annular groove 124, the compressed O-ring 122 will quickly relax into a smaller inner diameter shape engaging annular groove 124 providing the user with a tactile sensation. Preferably such tactile sensation will include both a vibration and auditory signal, indicating that the attachment 14 is in the proper position on motor assembly 12.

While the movement of O-ring 122 into annular groove 124 provides tactile sensation of the proper positioning of attachment housing 14 with respect to motor assembly 12, it will be appreciated that the attachment housing 14 is not positively locked to motor assembly 12. Rather, the configuration of internal cavity 118 closely matches the external configuration of coupling assembly 20 to create an interference fit sufficient to prevent accidental dislodging of attachment housing 14 from motor assembly 12. However, it will be understood that manual pulling along the longitudinal axis of attachment housing 14 will easily dislodge the attachment housing from motor assembly 12. In this preferred aspect, it is contemplated that the user will not have to operate any mechanical locking members to lock or unlock the attachment housing to the motor assembly thereby easing the operation for the end user. Accordingly, position of the attachment 14 relative to the motor assembly 12 may be calculated prior to assembly of the instrument 10. Because of this, the indicator marks maybe applied to the attachment 14 and motor assembly 12 at the component level before the instrument 10 is assembled.

In still another embodiment, the apertures 108 of the coupling assembly 20 may be replaced by one or more protuberances. Rather than inserting and aligning pins 112 as previously described, the protuberances may be aligned with the apertures 110 of the motor assembly 12. The protuberances may then engage the apertures 110 when the base 104 of the coupling assembly 20 is inserted into the motor assembly 12. Accordingly, the protuberances may align the coupling assembly 20 and the motor assembly 12 and may also prevent the coupling assembly 20 from rotating relative to the motor assembly 12. Furthermore, this A arrangement may provide sufficient structural strength to survive the loading created by the rotation of the tool 16 during surgery.

It is understood that alternative embodiments may reverse the arrangement so that the protuberances are located on the motor assembly 12 to engage the apertures 108 located on the coupling assembly 20, the apertures may be angled differently, and/or other engaging means may be used to achieve the same result. Likewise, variations of the protuberance and aperture approach described above may be used to fasten the attachment 14 to the coupling assembly 20.

Using the above described locking and indexing system, the relative positions that will be occupied by the motor assembly 12, attachment 14, and coupling assembly 20 with respect to one another may be determined before the instrument is assembled. Accordingly, alignment markings and other labeling/lettering may be applied at the component level and be in alignment when the instrument 10 is assembled. Furthermore, the locking and indexing system described above enables fabrication of housings while maintaining the alignment between any finger controls and the coupling assembly 20. In addition, the system securely attaches the coupling assembly 20 to the motor assembly 12 in a manner that may withstand with repeated loading caused by the rotation of the tool 16 during use.

While the invention has been particularly shown and described with reference to the preferred embodiment thereof, it will be understood by those skilled in the art that various changes in form and detail may be made therein without departing from the spirit and scope of the invention. For example, while the present illustrative embodiments show pneumatic powered motors, it is contemplated that the improvements described herein may be applied in an equal fashion to other motors, such as electric motors operating on AC or DC currents and ultrasonic motors run by piezo-electric or magneto-strictive forces. Furthermore, the various means described for connecting various housings or components may be replaced by other suitable means in ways known to those in the art. Therefore, the claims should be interpreted in a broad manner, consistent with the present invention.

What is claimed is:

1. A surgical instrument comprising:
    a collet including a first engaging means and a third engaging means;
    a motor assembly operable to receive the collet in a cavity, the cavity including a second engaging means operable to engage the first engaging means to align and prevent rotation of the collet relative to the motor assembly;
    a locking element rotatable about an axis of the collet, the locking element operable to secure the collet to the motor assembly; and
    an attachment having a fourth engaging means operable to engage the third engaging means;
    wherein one of the third and fourth engaging means is a groove and the remaining third or fourth engaging means is a protuberance.

2. The surgical instrument of claim 1 wherein the first and second engaging means are first and second apertures, respectively, and wherein the instrument further comprises a rigid member operable to fit into a cavity formed by the first and second apertures.

3. The surgical instrument of claim 1 wherein one of the first and second engaging means is an aperture and the other engaging means is a protuberance.

4. The surgical instrument of claim 1 wherein the attachment includes an internal cavity shaped substantially like an exterior of the collet.

5. The locking system of claim 1 wherein the locking element includes threads operable to engage corresponding threads on the motor assembly.

6. The locking system of claim 1 wherein the collet further comprises a base portion proximate to the motor assembly, wherein the base portion is operable to engage the locking element.

7. The locking system of claim 6 wherein an outer diameter of the base portion is larger than an inner diameter of the locking element, so that the locking element cannot slide past the base portion.

8. A locking system for a surgical instrument comprising:
    a collet having a first engagement element and a fourth engagement element;
    a motor assembly having a second engagement element corresponding to the first engagement element, wherein the first and second engagement elements are operable to align and prevent rotation of the collet relative to the motor assembly;
    an attachment having a third engagement element operable to engage the fourth engagement element on the collet; and
    a slidable locking member operable to secure the collet to the motor assembly,
    wherein one of the third and fourth engagement elements is a protuberance and the remaining third or fourth engagement element is an aperture operable to receive the protuberance.

9. The locking system of claim 8 wherein the first and second engagement elements are apertures operable to form a cavity around a rigid fastening member.

10. The locking system of claim 8 wherein one of the first and second engagement elements is a protuberance and the remaining first or second engagement element is an aperture operable to receive the protuberance.

11. The locking system of claim 8 wherein the attachment includes an internal cavity having a configuration substantially matching an external configuration of the collet.

12. The locking system of claim 8 wherein the attachment is operable to rotate at least partially around an axis of the collet, wherein the rotation is operable to lock or unlock the collet.

13. A surgical instrument comprising:
   a collet including a first engaging means and a third engaging means;
   a motor assembly operable to receive the collet in a cavity, the cavity including a second engaging means operable to engage the first engaging means to prevent rotation of the collet relative to the motor assembly;
   a locking element rotatable about an axis of the collet, the locking element operable to secure the collet to the motor assembly; and
   an attachment having a fourth engaging means operable to engage the third engaging means, wherein the motor assembly and the attachment include marks operable to indicate whether the collet is locked or unlocked.

14. A collet for insertion into a cavity of a surgical instrument, the collet comprising:
   a distal portion having an opening for receiving a tool;
   a first fastening element for accepting a second fastening element of an attachment, wherein one of the fastening elements is a protuberance and the other an aperture;
   a proximal portion with a first alignment element for engaging a second alignment element present in the cavity, the first alignment element and the second alignment element operable to align and prevent rotation of the collet and the surgical instrument; and
   a locking member rotatable about an axis of the collet, the locking member for securing the collet to the surgical instrument.

15. The collet of claim 14 wherein the first alignment element is an aperture operable to receive a rigid member.

16. The collet of claim 14 wherein the first alignment element is a protuberance for insertion into an aperture.

17. The collet of claim 14 wherein the locking member is translatable along an axis of the collet.

18. The collet of claim 14 wherein the locking member includes threads operable to engage corresponding threads on the surgical instrument.

19. The collet of claim 14 wherein the first fastening element is a protuberance for insertion into an aperture formed in the attachment.

20. A method for assembling a surgical instrument, the method comprising:
   aligning a first anti-rotation element of a collet with a corresponding second anti-rotation element on a motor assembly;
   inserting the collet into a cavity in the motor assembly, whereby the corresponding first and second anti-rotation elements are engaged; and
   securing the collet to the motor assembly using a locking member;
   whereby an attachment can be fastened to the collet in a position determined by the engaged anti-rotation elements.

21. The method of claim 20 further including sliding the locking member over the collet in the direction of the motor assembly.

22. The method of claim 20 further including inserting a tool into a receptacle in the collet and rotating at least a portion of the collet to secure the tool.

23. The method of claim 22 wherein rotating the portion of the collet includes rotating the attachment so that a mark on the attachment aligns with a corresponding mark on the motor assembly.

* * * * *